US006486669B1

United States Patent
Sinkus et al.

(10) Patent No.: US 6,486,669 B1
(45) Date of Patent: Nov. 26, 2002

(54) MR ELASTOGRAPHY METHOD

(75) Inventors: Ralph Sinkus, Hamburg (DE); Dietrich Holz, Henstedt-Ulzburg (DE); Michael W. P. Dargatz, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/743,659

(22) PCT Filed: May 8, 2000

(86) PCT No.: PCT/EP00/04218
§ 371 (c)(1),
(2), (4) Date: Jan. 12, 2001

(87) PCT Pub. No.: WO00/70362
PCT Pub. Date: Nov. 23, 2000

(30) Foreign Application Priority Data

May 14, 1999 (DE) .......................................... 199 22 214
Nov. 3, 1999 (DE) .......................................... 199 52 880

(51) Int. Cl.[7] ................................................. G01V 3/00
(52) U.S. Cl. ...................................... 324/307; 324/309
(58) Field of Search ................................. 324/309, 307, 324/306, 311, 312, 314, 300

(56) References Cited

U.S. PATENT DOCUMENTS 5,825,186 A * 10/1998 Ehman et al. ............... 324/309
5,899,858 A * 5/1999 Muthupillai et al. ........ 324/307
6,246,895 B1 * 6/2001 Plewes ........................ 324/309

FOREIGN PATENT DOCUMENTS

EP 0708340 A1 4/1996

OTHER PUBLICATIONS

Muthupillai et al "Three Dimensional Magnetic Resonance Elastography with Mult–Axis Encoding" Proceedings of the International Society of MR in Medicine, Fifth Scientific Meeting, Vancouver Canada Apr. 12–18, 1997.*
"Image Analysis Techniques for Magnetic Resonance Elastography", By A. Manduca et al, Porceedings of ISMRM, 1997. p. 1905.

* cited by examiner

Primary Examiner—Louis Arana
(74) Attorney, Agent, or Firm—John Vodopia

(57) ABSTRACT

MR elastography is a non-invasive imaging modality in which a visco-elastic region (such as the human breast) is excited by mechanical waves. Present-day approaches are based on transverse waves and on other assumptions which produce artefacts when there are longitudinal wave or reflections within that region. The invention is based on the insight that the results of the MRE measurement are the time-independent solution of the partial differential equations describing exactly the behavior of mechanical waves in visco-elastic material (even for longitudinal waves and in a reflecting environment). Therefore, Young's modulus contained in these equations can be calculated. Moreover, it is proposed to use (predominantly) longitudinal waves. Longitudinal waves are capable of penetrating the human breast, whereas transverse waves are not.

11 Claims, 4 Drawing Sheets

MR ELASTOGRAPHY METHOD

Figure 1:
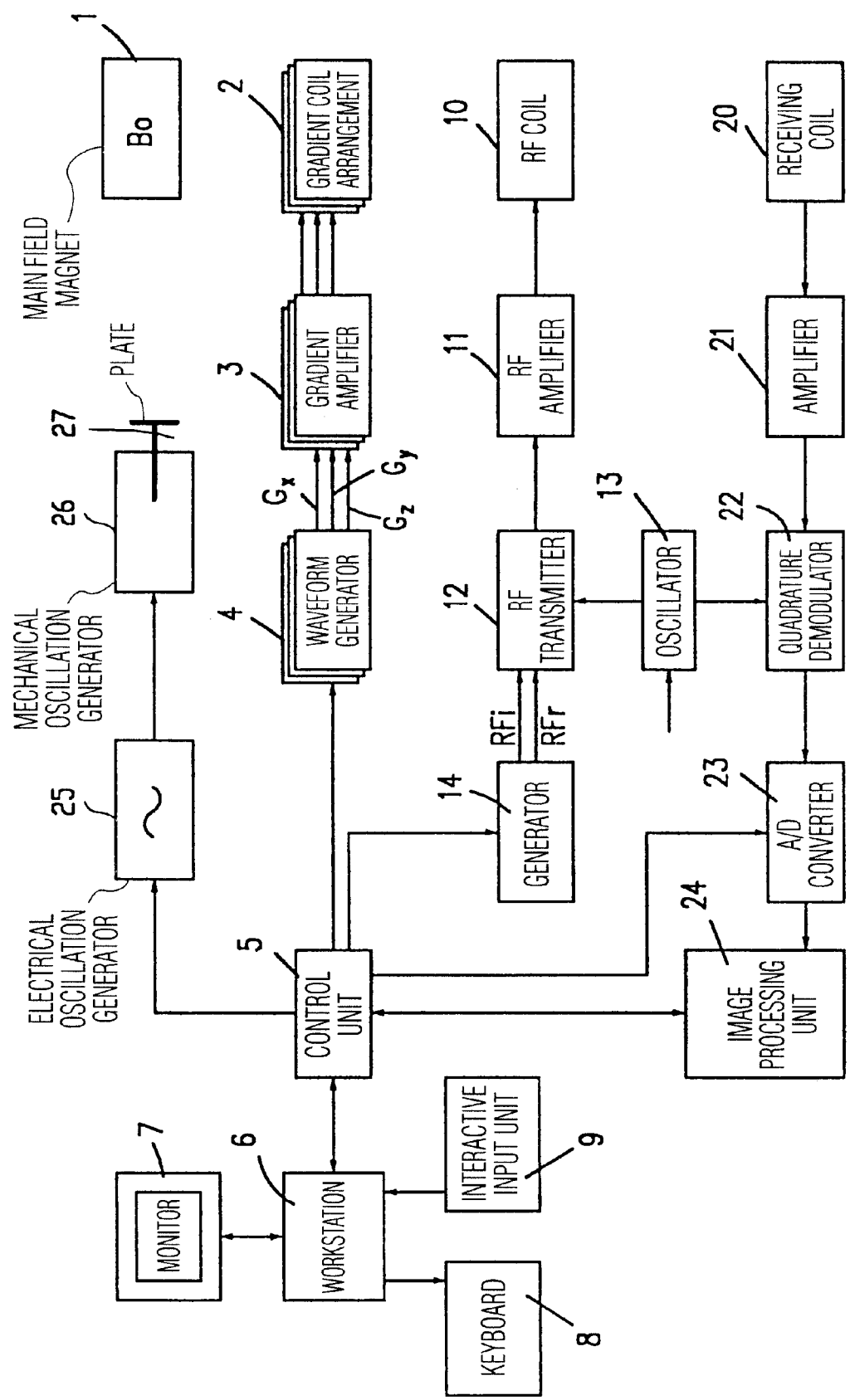

The invention relates to a method of determining mechanical parameters of an object to be examined, which method includes the steps of:

a) generating mechanical oscillations in the object to be examined, b) exciting the nuclear magnetization in conjunction with a magnetic gradient field which is synchronized with the mechanical oscillations, and receiving the MR signals arising in the object to be examined in order to produce an MR phase image, c) changing the direction of the gradient of the gradient field and/or the phase difference between the mechanical oscillations and the gradient field, d) repeating the steps a to c) a number of times, e) determining, on the basis of the MR phase images, the deflection of the nuclear spins from their state of equilibrium which is caused by the mechanical oscillations, and calculating at least one mechanical parameter in dependence on the deflection.

Methods of this kind are known as MRE methods (MRE= Magnetic Resonance Elastography). Such a method utilizes the fact that the phase in an MR image of the object to be examined changes due to the mechanical oscillations active therein. The extent of such changes is dependent on the deflection (i.e. the shift out of the state of equilibrium) caused by the mechanical oscillation. Information concerning given mechanical parameters of the tissue, for example concerning the elasticity, can thus be derived from the MR phase images, i.e. images reproducing the phase of the nuclear magnetization.

EP-A 708 340 discloses an MR elastography method of this kind. Therein, first two MR phase images are formed of a slice of the object to be examined. The direction of the gradient of a magnetic gradient field which is synchronized with the mechanical oscillations is the same in both images, but the phases of this periodic gradient are 90° offset in relation to the mechanical oscillation. Subsequently, further pairs of MR phase images are produced in which the periodic gradient extends perpendicularly to the gradient direction for the first pair. Subsequently, the direction of the mechanical oscillation in the object is changed and further sets of MR phase images are acquired.

The wavelength for the various pixels can be determined from each pair of MR phase images. The modulus of elasticity (Young's modulus) can be calculated from the wavelength when the propagation speed of the wave in the object to be examined and the density thereof are known.

In another method which is known from Proceedings of ISM 1997, p. 1905, Vancouver, the phase of the deflection is determined from a series of MR phase images and therefrom the modulus of elasticity is calculated for each individual pixel.

It is a common aspect of the known methods that they yield satisfactory results only if no reflections occur in the object to be examined and if only transverse oscillations propagate in the object. However, in a real object to be examined, for example the body of a patient, reflections are inevitable and a purely transverse wave propagation cannot be achieved either. Moreover, it is known that longitudinal mechanical oscillations can penetrate deeper into a body, so that it would be desirable per se to achieve longitudinal propagation for an as large as possible part of the mechanical vibration energy.

It is an object of the present invention to conceive a method of the kind set forth in such a manner that the mechanical parameters of the object can be reliably determined also in the case of longitudinal wave propagation or reflections in the object to be examined.

This object is achieved according to the invention by determining the amount and the phase of the deflection in a three-dimensional zone for three mutually perpendicular directions and by calculating at least one mechanical parameter from these values of the deflection and from their spatial derivatives in at least a part of the three-dimensional zone.

The invention is based on the recognition of the fact that the propagation of mechanical waves in visco-elastic media can be described by a partial differential equation whose solution for each voxel is determined by the amount and phase of the deflection in three mutually perpendicular directions as well as by the spatial derivatives of the deflection. When these quantities have been determined for each voxel, the measured values can be inserted in the differential equation and at least one of the mechanical parameters contained in said equation can be calculated therefrom.

Thus, it does not suffice to determine the deflection for only a single direction in space. It is not sufficient either to determine the deflection in all three spatial directions for one slice only, not even if a mechanical parameter (for example, the modulus of elasticity) is to be determined for this slice only. This is because, as is known, a spatial derivative of the deflection in the direction perpendicular to the slice can be determined only if the deflection is determined also in zones outside the slice. The deflection, therefore, must be determined in a three-dimensional zone, i.e. the MR phase images should reproduce the spatial distribution of the phase of the nuclear magnetization in this three-dimensional zone.

When the mechanical oscillations act on the object to be examined in such a manner that essentially longitudinal oscillations occur in conformity with claim 2, a larger penetration depth is obtained for the oscillations so that the mechanical parameters, for example of the tissue in a human body, can be determined in a larger zone.

The version of the invention as disclosed in claim 3 ensures that during each repeated excitation of the nuclear magnetization the mechanical oscillations are associated exactly in time with the gradient fields produced in conjunction with the excitation of the nuclear magnetization, notably with the gradient field synchronized with the mechanical oscillations.

The invention is based on the assumption that a series of MR phase images is formed of a three-dimensional zone so that comparatively long measuring times occur. In order to ensure that these measuring times are not prolonged further by waiting for the decaying of the nuclear magnetization in the excited zone after an excitation, the slices constituting the three-dimensional zone to be excited are excited by means of a multi-slice method as disclosed in claim 4.

A preferred version of the invention is disclosed in claim 5. Even though other mechanical parameters can also be calculated, for example, the density of the tissue, the Poisson number or the attenuation of the wave by the tissue, the modulus of elasticity is the most relevant parameter for the diagnosis. The elasticity is the mechanical parameter to be determined by a physician during the palpation of the tissue.

Particularly advantageous is the determination of the modulus of elasticity during examination of the mamma in conformity with claim 6.

Claim 7 describes a device for carrying out the method according to the invention.

In accordance with claim 8 the wave and the magnetic gradient field synchronized therewith vary sinusoidally in time. Even though a different periodic variation is also feasible, for example a sawtooth, delta or squarewave variation, the sinusoidal variation offers advantages. As many as 6 different mechanical parameters can be calculated on the basis of the measurement results.

The further embodiment in conformity with claim 9 enables calculation of more than 6 different mechanical parameters. In accordance with claim 10 the modulus of elasticity and one further mechanical parameter, for example, the attenuation coefficient, can then be calculated, even when one of these two parameters (or both parameters) is (are) not an isotropic quantity.

Claim 11 describes a computer program which is suitable for the method according to the invention.

Figure 2:
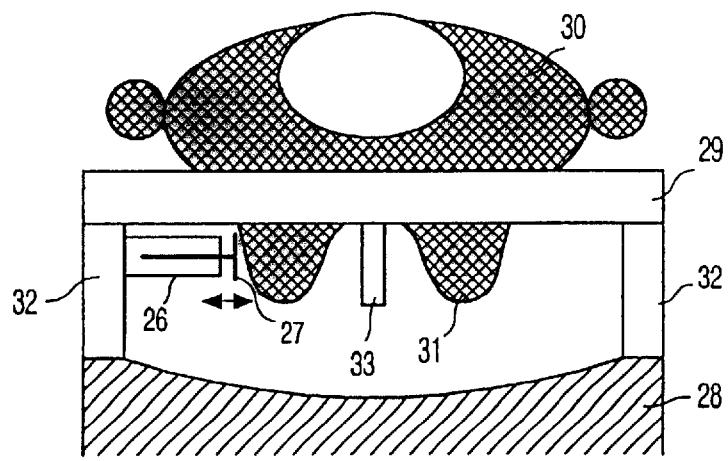
Figure 7:
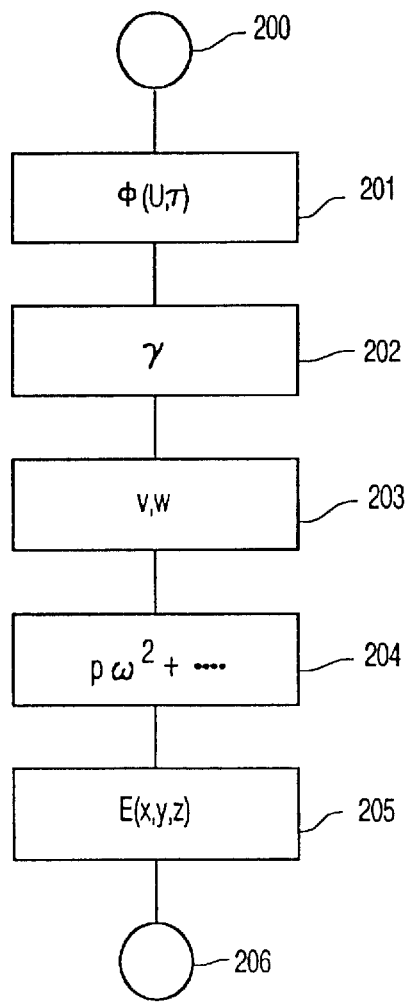
Figure 3:
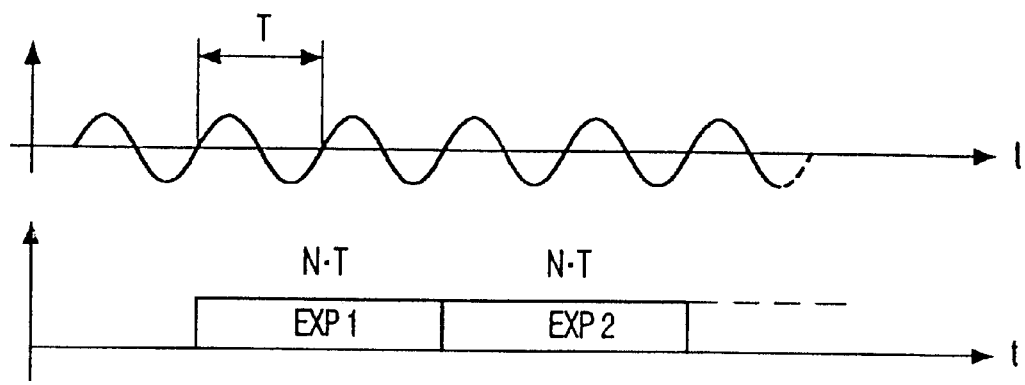
Figure 4:
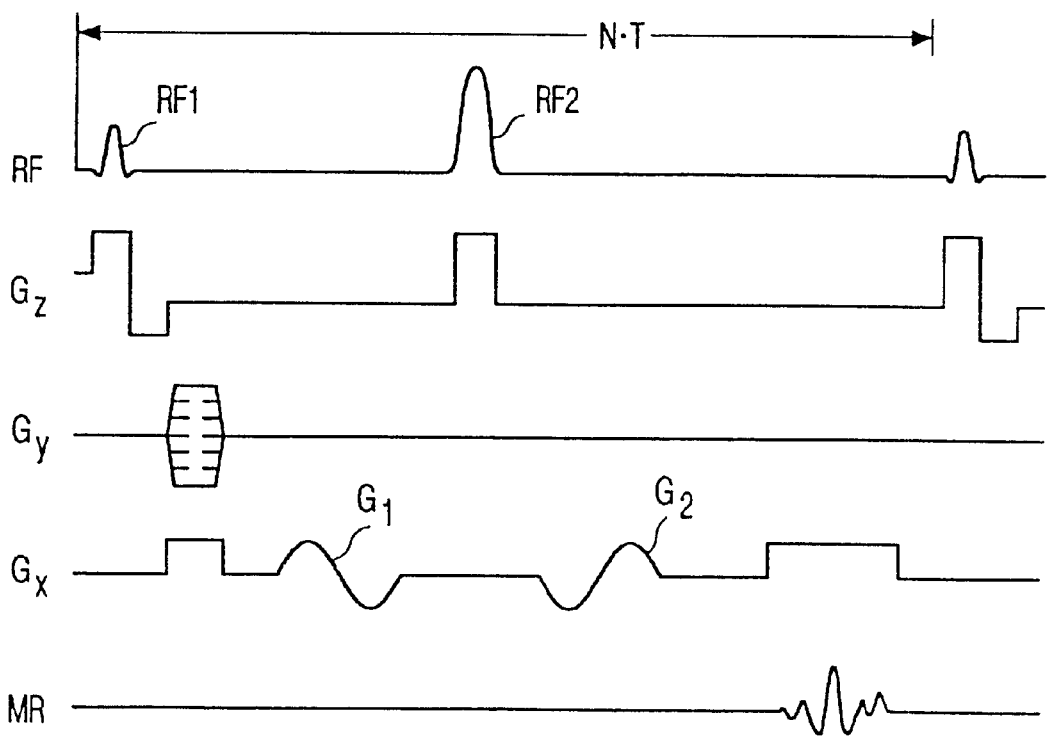
Figure 5:
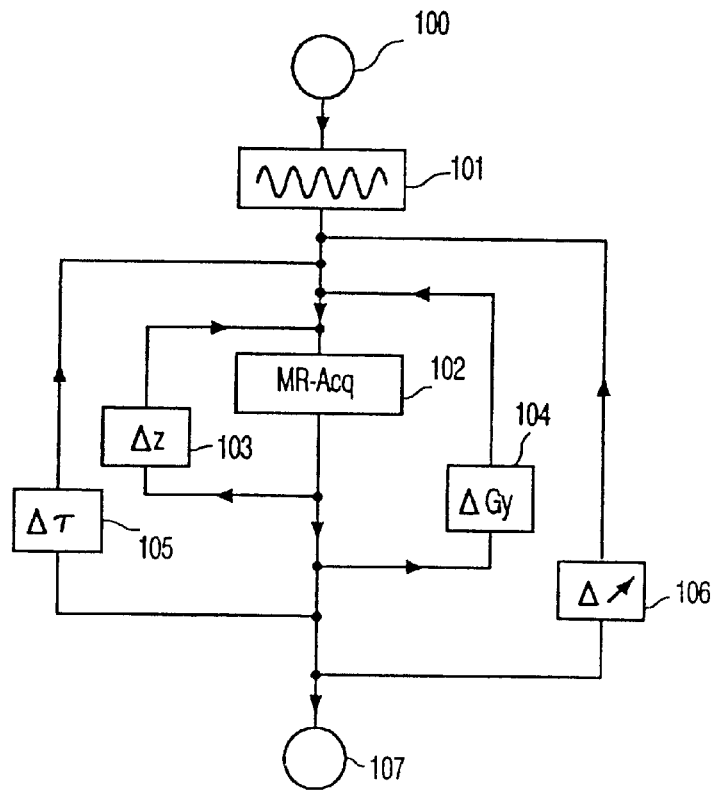
Figure 6:
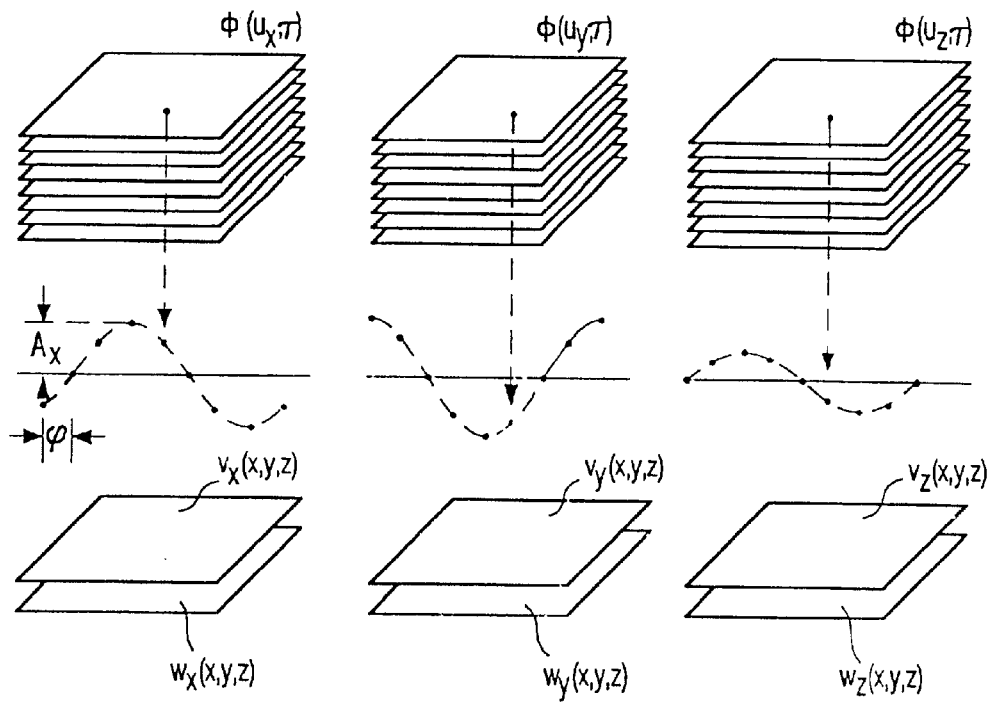

The invention will be described in detail hereinafter with reference to the drawings. Therein:

FIG. 1 shows a block diagram of a device for carrying out the method according to the invention, FIG. 2 shows a part of an examination apparatus suitable for this purpose, FIG. 3 shows the position in time of the mechanical oscillations and the MR experiments, FIG. 4 shows the execution in time of a single MR experiment, FIG. 5 shows a flow chart illustrating the MR acquisition method, FIG. 6 is a diagrammatic representation of a part of the evaluation process, and FIG. 7 shows a flow chart illustrating the evaluation process.

The reference numeral 1 in FIG. 1 denotes a diagrammatically represented main field magnet which generates, in an examination zone not shown, a steady, essentially uniform magnetic field which extends in the z direction and has a strength of, for example, 1.5 Tesla. Also provided is a gradient coil arrangement 2 which includes three coil systems whereby magnetic gradient fields $G_x$, $G_y$ and $G_z$, having a gradient in the x, the y and the z direction, respectively, can be generated. The currents for the gradient coil arrangement 2 are supplied by respective gradient amplifiers 3. Their variation in time is imposed by a waveform generator 4, that is, separately for each direction. The waveform generator 4 is controlled by an arithmetic and control unit 5 which calculates the variation in time of the magnetic gradient fields $G_x$, $G_y$ $G_z$ which is required for a given examination method and loads this variation into the waveform generator 4. During the MR examination these signals are read out from the waveform generator 4 and applied to the gradient amplifier system 3 which generates the currents required for the gradient coil system 2 on the basis thereof.

The control unit 5, moreover, co-operates with a workstation 6 which includes a monitor 7 for the display of MR images. Entries can be made via a keyboard 8 or an interactive input unit 9.

The nuclear magnetization in the examination zone can be excited by RF pulses from an RF coil 10 which is connected to an RF amplifier 11 which amplifies the output signals of an RF transmitter 12. In the RF transmitter 12 the (complex) envelopes of the RF pulses are modulated with the carrier oscillations which are supplied by an oscillator 13 and whose frequency corresponds to the Larmor frequency (amounting to approximately 63 MHz in the case of a main magnetic field of 1.5 Tesla). The arithmetic and control unit loads the complex envelope into a generator 14 which is coupled to the transmitter 12.

The MR signals generated in the examination zone are picked up by a receiving coil 20 and amplified by an amplifier 21. The amplified MR signal is demodulated in a quadrature demodulator 22 by two mutually 90° offset carrier oscillations of the oscillator 13, thus generating two signals which may be considered as the real part and the imaginary part of a complex MR signal. These signals are applied to an analog-to-digital converter 23 which forms MR data therefrom. MR images representing the nuclear magnetization in the examination zone are reconstructed from the MR data in an image processing unit 14. After treatment by a noise reduction filter these MR images are displayed on the monitor 7 and form the basis for the calculation of images (again in the image processing unit 24) which represent the variation in space of a mechanical parameter, for example the modulus of elasticity.

Moreover, the control unit 5 triggers an electrical oscillation generator 25 so as to generate a sinusoidal current of a fixed frequency in the range of between approximately 20 Hz and some 100 Hz. This oscillation is applied to a mechanical oscillation generator 26 and ensures that a piston with a plate 27 connected to its front end is made to perform a reciprocating, preferably sinusoidal motion in a direction perpendicular to the plane of the plate.

FIG. 2 shows mounted on the patient table unit 28 of the MR apparatus whose block diagram is shown in FIG. 1, a facility which is suitable for mamma examinations. This facility includes a supporting plate 29 which bears on the patient table unit in a manner not shown and on which the female patient 30 is accommodated; this supporting plate is provided with cut-outs for the breasts 31 of the patient in the prone position. Supports 32 for the mechanical oscillation generator 26 (shown only for the left-hand side) which are displaceable in the horizontal direction are provided so as to press a breast against an approximately central partition 33. Mechanical oscillations can thus be generated in the breast by means of a reciprocating motion of the piston plate 27.

FIG. 3 shows the association in time between the mechanical oscillations (first line) and the MR experiments (second line). The generating of the oscillations of duration T commences before the acquisition of MR data by the MR experiments. The aim is to achieve a state of equilibrium for the mechanical oscillations before the MR acquisition is started. Each of the successive MR experiments has a duration NT, where N is an integer. It is thus ensured that the mechanical oscillation has a defined phase position in relation to all MR experiments.

Each of the MR experiments, one of which is shown in FIG. 4, includes the excitation of the nuclear magnetization by at least one RF pulse and the acquisition of at least one MR signal, in this case being a spin echo signal. The use of spin echo signals offers the advantage that the MR signals are free from phase errors to a high degree.

The first line shows the RF excitation pulses, i.e. a 90° RF pulse RF1 and a 180° RF pulse RF2. Both pulses are accompanied by a slice selection gradient $G_z$ so that the nuclear magnetization is excited each time in one slice only.

FIG. 4 shows in part the typical execution of a spin echo experiment with a 90° RF pulse and a 180° RF pulse, RF1 and RF2, respectively, (first line) which are accompanied by a slice selection gradient $G_z$, the phase being encoded by a phase encoding gradient $G_y$, and the spin echo signal produced being read out in conjunction with a read-out gradient $G_x$. Instead of a spin echo acquisition, however, other MR acquisition schemes can also be used, for example as described in EP-A 708 340. The slice selection, phase encoding and read-out gradients need not necessarily coincide with the z, the y and the x direction, respectively, as shown in FIG. 4. It is only essential that they extend perpendicularly to one another.

The experiment additionally involves two gradient oscillations G1 and G2 which are situated to both sides of the 180° RF pulse, vary sinusoidally in time and whose period duration corresponds to the period duration T of the mechanical oscillation whereas their phase differences relative to the mechanical vibration differ exactly 180°. In FIG. 4 the sinusoidal gradients G1 and G2 extend in the x direction. In the further course of the method, however, they extend in the z direction or in the y direction instead. The gradient oscillations G1 and G2 change the phase of the spins deflected by the mechanical oscillation, the degree of change being dependent on the degree of deflection in the direction of the relevant gradient.

FIG. 5 illustrates the acquisition in time of the MR data. After the initialization (block 100), the piston is made to oscillate with continuous, sinusoidal oscillations which last throughout the MR acquisition (block 101). When such oscillations have become steady, in the block 102 a first MR experiment is performed in conformity with FIG. 4 and the MR signal thus produced (fifth line of FIG. 4) is acquired. When the duration NT of an MR experiment is short, for example 50 ms, the nuclear magnetization in the previously excited slice will not have decayed yet when the next MR experiment commences. Therefore, the MR experiment is repeated for a different slice which is offset in the z direction in this case (block 103). This means that merely the carrier frequency of the RF pulses RF1 and RF2 is changed in such a manner that the other slice is excited whereas the variations in time in the second through fifth line of FIG. 4 remain the same. The loop including the blocks 102 and 103 is completed as many times as there are slices present in the three-dimensional zone to be examined, for example 20 times, each time a different slice being excited.

Subsequently, the phase encoding gradient is changed in step 104 and all slices are excited again and the spin echo signals generated therein are acquired. The phase encoding gradient is changed as many times as there are phase encoding steps required, for example 128 or 256 times. After that the MR data of all slices will have been acquired so that therefrom an MR image can be reconstructed which reproduces the phase of the nuclear magnetization distribution in the three-dimensional zone formed by the slices.

After the MR data for the first MR phase image of the three-dimensional zone have thus been acquired, in the step 105 a shift in time is performed between the MR experiments and the mechanical oscillation, that is, in such a manner that the beginning of an MR experiment no longer coincides (as shown in FIG. 3) with the zero crossing of the mechanical oscillation, but is offset a fraction of a period T, for example T/8, with respect thereto (step 105). Subsequently, the loop with the steps 102, 103, 104 is completed again, so that a further MR phase image of the three-dimensional zone examined is obtained. The two MR phase images deviate from one another only in the regions in which the tissue, or the spins excited therein, has (have) been deflected in the x direction. Subsequently, further MR phase images are generated, the offset in time then being changed to 2T/8, 3T/8 . . . 7T/8. Finally, the MR data will have been acquired for eight MR phase images which have been influenced to a different extent by the deflection of the spins in the x direction but are otherwise identical.

In order to enable measurement of the deflection in a direction other than the x direction, the sinusoidal gradients $G_1$ and $G_2$ are generated (block 106) in a direction other than the x direction of FIG. 4, for example in the y direction so that, after completion of the described loops with the step 102, 103, 104, 105, there is available a set of MR phase images of the three-dimensional zone which has been influenced by the deflection of the spins in the y direction. Finally, the foregoing is repeated for the z direction (the sinusoidal gradients $G_1$ and $G_2$ are applied in the z direction) so that ultimately there is available a further set of eight MR phase images which are dependent on the deflection of the spins in the z direction. This completes the acquisition process (block 107).

The processing of the MR data will be described in detail with reference to FIG. 7. After the initialization in the block 100, in the step 201 MR phase images are formed from the acquired MR data as has already been explained. The demodulation of the MR signal with two 90° offset oscillations in the demodulator 22 (FIG. 1) yields two signals which may be considered as the real part and the imaginary part of a complex signal. A first image can be reconstructed from the real parts of the MR signals and a second image from the imaginary parts. For each voxel the phase can be calculated from the real part and the imaginary part, thus yielding an MR phase image. The calculation of the MR phase images may commence already during the acquisition of the MR data.

The attenuation of the mechanical waves in the examination zone can be determined in the step 202. To this end, the propagation of the wave in the tissue is tracked along a ray in the direction of the applied mechanical oscillation, it being assumed for the sake of simplicity that it acts on the body either in the x, the y or the z direction. The phase of a point on the ray will then change sinusoidally due to the deflection. At another point on the ray, being situated further from the point of application of the mechanical waves, there will also be a sinusoidal variation of the MR phase; however, the amplitude thereof will be lower because of the attenuation of the wave. An attenuation coefficient y can be calculated from the variation of the amplitude along the ray.

In the step 203 the amount and the phase are determined for each of the three spatial directions and for each of the individual voxels of the three-dimensional examination zone.

This is diagrammatically illustrated in FIG. 6. The upper row shows diagrammatically three sets of MR images whose phase is dependent on the deflection in x, y and z. The images are shown in simplified form as two-dimensional images, even though each image represents the MR phase in a three-dimensional zone. In each of the eight MR images belonging to a set the phase is considered in the same pixel. Eight points of support for the variation in time of the phase in the relevant pixel are derived from the eight images. Because of the sinusoidal deflection, the variation in time is sinusoidal as is diagrammatically indicated on the second line. However, a positive or a negative continuous component may also be superposed on the sinusoidal variation.

Subsequently, a Fourier transformation is performed over the phase defined by eight points of support, i.e. the sine function extending through the points of support or as closely as possible to these points of support is determined. The amount of the sine function is proportional to the deflection of the voxel and its phase defines the position in time of the sinusoidal oscillation at the relevant voxel in relation to an arbitrary reference phase. From the amount $A_x$ and the temporal phase $\phi$ of the eight images, with gradients $G_1$ and $G_2$ extending in the x direction, a complex value $u_x$ can be defined as follows for the deflection in the relevant voxel:

$$A_x e^{j\phi} = u_x = v_x + j w_x \qquad (1)$$

Therein, $v_x$, and $w_x$, represent the real part and the imaginary part, respectively, of the complex quantity $u_x$.

The foregoing is repeated for all voxels of the eight images, thus yielding two images (defined for a three-dimensional zone) which reproduce the real part $v_x$ and the imaginary part $w_x$, respectively, of the deflection. The same is done for the sets of MR phase images acquired with a sinusoidal gradient extending in the x direction and in the z direction and whose phase, therefore, is defined by the deflection in the z direction and the z direction, respectively. Thus, at the end of the step 203 there are obtained three images which reproduce the real part $v_x$, $v_y$ and $v_z$ of the deflection in the x direction, the y direction and the z direction, respectively, and three images which reproduce the imaginary part $w_x$, $w_y$ and $w_z$ of the deflection.

The next process step 204 is based on the recognition of the fact that the values of the deflection $u_x$, $u_y$ and $u_z$ thus found represent solutions of the partial differential equation describing the deflection in the relevant voxels. Therefore, the values found for deflection in the step 204 are inserted in the differential equation in order to enable calculation of the mechanical parameters of the tissue, for example its modulus of elasticity.

The partial differential equation describing the propagation of a wave in a viscous, elastic medium is as follows:

$$\rho \frac{\partial^2 U}{\partial t^2} - \gamma \frac{\partial U}{\partial t} = \frac{E}{2(1+\sigma)} \Delta U + \frac{E}{2(1+\sigma)(1-2\sigma)} \nabla(\nabla U) \qquad (2)$$

In this differential equation $\rho$ represents the density in the examination zone, $\gamma$ represents the attenuation of the wave as determined in the step 202, $\sigma$ represents the so-called Poisson number (approximately 0.49 for human tissue) and E represents the modulus of elasticity. U is the vector of the deflection in the x direction, the y direction and the z direction. $\nabla$ represents the so-called Nabla operator, i.e. a vector for which it holds that:

$$\nabla = \frac{\partial}{\partial x}, \frac{\partial}{\partial y}, \frac{\partial}{\partial z} \qquad (3)$$

$\Delta$ is the so-called Laplace operator for which it is known that it holds that:

$$\Delta = \nabla \cdot \nabla \qquad (4)$$

The formulation $$U = u \cdot e^{j\omega t} \qquad (5)$$

wherein u is an exclusively location-dependent vector and $\omega$ represents the (angular) frequency of the mechanical oscillation, yields the following differential equation after insertion in the equation (2):

$$-\rho \omega^2 u - j\omega \gamma u = \frac{E}{2(1+\sigma)} \Delta u + \frac{E}{2(1+\sigma)(1-2\sigma)} \nabla(\nabla u) \qquad (6)$$

Therein, u represents the vector of the deflection whose components in the x, the y and the z direction are obtained as $u_x$, $u_y$ and $u_z$ in conformity with the equation $$u = u_x, u_y, u_z \qquad (7)$$

Each vector component itself can be represented as a complex quantity in conformity with the relation $$u_x = v_x + jw_x; \; u_y = v_y + jw_y; \; u_z = v_z + jw_z \qquad (8)$$

It will be apparent from the foregoing that, even though the equation (6) represents only a single differential equation for u, six equations can be derived therefrom, i.e. three for each of the three directions and each time two for the real part and the imaginary part. Assuming that in addition to the angular frequency $\omega$ the values of $\sigma$, $\gamma$ and $\rho$ in the relevant voxel are also known, it suffices to insert the measured deflections in only a single one of these six equations and to calculate therefrom the modulus of elasticity E in the relevant voxel. The equation $$-\rho \omega^2 v_x + \gamma \omega w_x = \qquad (9)$$
$$\frac{E}{2(1+\sigma)} \left( \frac{\partial^2 v_x}{\partial x^2} + \frac{\partial^2 v_x}{\partial y^2} + \frac{\partial^2 v_x}{\partial z^2} \right) + \frac{E}{c} \left( \frac{\partial^2 v_x}{\partial x \partial x} + \frac{\partial^2 v_y}{\partial x \partial y} + \frac{\partial^2 v_z}{\partial x \partial z} \right)$$

thus represents the equation for the real part of the x component. Therein, c is a constant for which it holds that:

$$c = 2(1+\sigma)(1-2\sigma) \qquad (10)$$

The equation (9) shows that even in this simplest case it is necessary to know $w_x$, $v_x$, $v_y$, $v_z$ and their spatial derivatives in the x, the y and the z direction. Therefore, for this case all three components of the deflection according to real part and imaginary part or amount and phase should also be known, and also the spatial derivative of these quantities in the x, the y and the z direction. Thus it is necessary that the deflections are known in a three-dimensional zone, even when the modulus of elasticity is to be calculated for a two-dimensional zone only. In order to enable the spatial derivative or the differential quotient to be determined in the x, the y and the z direction, it is effective to approximate (for all three spatial directions) the variation of the complex deflections v and w as determined in the step 203 by means of envelopes which can be differentiated at least twice, so that the derivatives can be numerically calculated.

By inserting the values thus found for the deflections of $w_x$, $v_x$, $v_y$, $v_z$ and their numerical derivatives as well as the values for $\sigma$, $\rho$ and $\gamma$ which are assumed to be known, the modulus of elasticity can be calculated by means of the equation 9, that is, for all voxels of the three-dimensional zone (except for those voxels which are situated directly at the edge, so that the spatial derivatives for these voxels cannot be simply calculated).

After the values E for the voxels of the examination zone have thus been calculated in the step 204, images representing the spatial variation of the modulus of elasticity in various slices of the examination zone can be derived therefrom (block 205). The process is then terminated (block 206).

It has been assumed in the foregoing that the modulus of elasticity is an isotropic quantity, so that only one of said six equations is to be solved in order to determine the modulus of elasticity E. However, if this condition is not satisfied, in conformity with $$E = \begin{vmatrix} e_{xx} & e_{xy} & e_{xz} \\ e_{yx} & e_{yy} & e_{yz} \\ e_{zx} & e_{zy} & e_{zz} \end{vmatrix} \qquad (11)$$

E is a tensor of second order (i.e. a matrix) whose 9 tensor elements $e_{xx} \ldots e_{zz}$ are to be inserted into the system of equations. Assuming that this tensor is symmetrical, i.e. that the conditions $$e_{yx} = e_{xy}; \; e_{zx} = e_{xz}; \; e_{zy} = e_{yz} \qquad (12)$$

are satisfied, the number of unknown tensor elements is reduced to six. These elements can be calculated from the previously mentioned six equations when the other parameters, such as the Poisson number, attenuation and density, are known. Transformation on the main axes then yields a tensor in which only the diagonal elements deviate from zero. Moreover, this transformation yields the angles at which the elasticity is maximum and minimum, respectively. These values are also of clinical interest.

For the described reconstruction method given tissue parameters were assumed to be known and constant throughout the object, i.e. the density ρ, the Poisson number σ and the attenuation coefficient γ. The assumption of a constant density as well as a constant Poisson number is theoretically justified. As regards the attenuation coefficient, however, it is known that it differs for different types of tissue and that these variations may be significant.

If at least one of these parameters, for example, the attenuation coefficient γ, is to be determined in addition to the above-mentioned tensor elements of the modulus of elasticity, the method described thus far cannot be simply carried out, because at least seven unknowns must be determined from the six results of the measurements. In order to enable additionally the determination of the six tensor elements of the attenuation coefficient (assuming that, like the modulus of elasticity, it has only six mutually independent tensor elements), instead of a single sinusoidal oscillation use is made of a mixture of at least two sinusoidal oscillations, both for the mechanical excitation of the object as well as for the gradients $G_1$ and $G_2$.

Thus, the oscillator is driven with two frequencies simultaneously, i.e. the variation in time of the oscillator oscillation S(t) is $$S(t) = a1 \sin(\omega 1 t) + a2 \sin(\omega 2 t) \quad (13)$$

where $a_1$ and $a_2$ are the amplitudes of the oscillations of the frequencies $\omega_1$ and $\omega_2$. Thus, the object is also simultaneously excited to two frequencies. Because two mechanical waves of different frequencies are thus present in the object, the gradient $G_1(t)$ which encodes the motion (see FIG. 4) and renders the MR sequence sensitive to motion must also be composed of two frequencies, i.e.

$$G1(t) = b1 \sin(\omega 1 t) + b2 \sin(\omega 2 t) \quad (14)$$

wherein $b_1$ and $b_2$ are the amplitudes of the oscillations of the frequencies $\omega_1$ and $\omega_2$ It is advantageous to choose:

$$\omega 2 = 2\omega 1 = 2\omega \quad (15)$$

As a result, the variations of the phase in the individual pixels (see FIG. 6) resulting from these measurements can be determined while using no more points of support (for example, eight)—with the same quality—as in the case of a purely sinusoidal oscillation. Moreover, $a_1 = a_2$ and possibly also $b_1$ and $b_2$ can be chosen.

The described reconstruction method utilizes the oscillation, measured by means of MR, of each voxel within the 3D volume observed. This oscillation is sampled with typically 8 values over the period of time of an oscillation (T=2π/ωs). A Fourier transformation of this oscillation produces the desired quantities for solving the differential equation system, i.e. amplitude and phase at the frequency for each voxel. Because of the additional excitation at the frequency 2ω and the adaptation of the variation in time of the gradient, the information available at the frequency 2ω can thus also be used. During the measurement of 8 values for one oscillation period 2π/ω, the Fourier transformation provides information for the frequencies ω, 2ω, 3ω and 4ω.

Because the mechanical excitation and the measurement take place at two frequencies and the mixed information is separated by the Fourier transformation at a later stage, the solutions for the wave equation are obtained for two frequencies. Instead of the equation (6) two systems of equations are thus obtained:

$$-\rho\omega_1^2 u_1 - j\omega_1\gamma u_1 = \frac{E}{2(1+\sigma)}\Delta u_1 + \frac{E}{2(1+\sigma)(1-2\sigma)}\nabla(\nabla u_1) \quad (16)$$

and $$-\rho\omega_2^2 u_2 - j\omega_2\gamma u_2 = \frac{E}{2(1+\sigma)}\Delta u_2 + \frac{E}{2(1+\sigma)(1-2\sigma)}\nabla(\nabla u_2) \quad (17)$$

which can be linked. It is thus possible to determine not only the elasticity tensor but also the attenuation tensor. In this context it is assumed that both desired quantities are not dependent on frequency. This assumption is justified in the relevant frequency range of from approximately 50 to 400 Hz. However, it is also possible to determine the elasticity tensor twice with both systems of equations. The signal-to-noise ratio in the images is enhanced by averaging over the values found.

What is claimed is:

1. A method of determining mechanical parameters of an object to be examined, the method comprising:
    generating mechanical oscillations in the object to be examined;
    exciting nuclear magnetization in conjunction with a magnetic gradient field (GI, GZ) which is synchronized with the mechanical oscillations, and receiving the MR signals arising in the object to be examined to form an MR phase image;
    changing a direction of a gradient of the gradient field and/or a phase difference between the mechanical oscillations and the gradient field,
    repeating the generating, exciting, and changing, respectively, a number of times; and
    determining, on the basis of the MR phase images, a deflection of nuclear spins from their state of equilibrium caused by the mechanical oscillations, and calculating at least one mechanical parameter in dependence on the deflection, wherein the at least one mechanical parameter includes the determination of an amount and phase of the deflection (U) in a three-dimensional zone for three mutually perpendicular directions, and the calculation of the at least one mechanical parameter (E) from the amount and phase of the deflection and from their spatial derivatives in at least a part of the three-dimensional zone.

2. The method as claimed in claim 1, further comprising:
    exciting essentially longitudinal oscillations in the object to be examined.

3. The method as claimed in claim 1, wherein multiple repetitions of the excitation of the nuclear magnetization are performed while continuously generating the mechanical oscillations in the object to be examined such that a distance in time between two repetitions is an integer multiple of a period of the mechanical oscillations.

4. The method as claimed in claim 1, further comprising:
    exciting mutually parallel slices, the excitation of a slice being followed by the excitation of other slices before the relevant slice is excited again.

5. The method as claimed in claim 1, wherein the calculation of the at least one mechanical parameter calculating a modulus of elasticity.

6. The method as claimed in claim 5, wherein the calculation is used for examinations of a mamma.

7. A device to determine mechanical parameters of an object to be examined comprising:

an MR apparatus;

a mechanical oscillation generator;

an evaluation unit;

a generator which determines the variation in time of magnetic gradient fields; and a control unit which controls the MR apparatus, the generator, the oscillation generator and the evaluation unit.

8. The device as claimed in claim 7, wherein the oscillation generator and the generator generate a temporally sinusoidal oscillation.

9. The device as claimed in claim 7, wherein the oscillation generator and the generator excite an oscillation which contains a mixture of at least two sinusoidal oscillations, ratio of the frequencies of the two sinusoidal oscillations being an integer.

10. The device as claimed in claim 9, further comprising:

a calculating unit to calculate a modulus of the elasticity (E) and a an attenuation coefficient ($\gamma$).

11. A computer program for a control unit which acts on an MR apparatus, an oscillation generator and an evaluation unit to carry out the method of determining mechanical parameters of an object to be examined, comprising:

generating mechanical oscillations in the object to be examined;

exciting nuclear magnetization in conjunction with a magnetic gradient field which is synchronized with the mechanical oscillations, and receiving the MR signals arising in the object to be examined to form an MR phase image;

changing a direction of a gradient of the gradient field and/or a phase difference between the mechanical oscillations and the gradient field, repeating the generating, exciting, and changing, respectively, a number of times; and determining an amount and phase of deflection in a three-dimensional zone for three mutually perpendicular directions, and calculating at least one mechanical parameter from the amount and phase of the deflection and from their spatial derivatives in at least a part of the three-dimensional zone.

* * * * *